(12) United States Patent
Collingwood et al.

(10) Patent No.: US 6,329,519 B1
(45) Date of Patent: Dec. 11, 2001

(54) INTERMEDIATES FOR OLIGONUCLEOTIDE SYNTHESIS

(75) Inventors: Stephen Paul Collingwood, Crawley; Heinz Ernst Moser, Horsham, both of (GB); Karl-Heinz Altmann, Reinach (CH); Mark Edward Douglas, Macclesfield (GB)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/202,294

(22) PCT Filed: Jun. 3, 1997

(86) PCT No.: PCT/GB97/01490

§ 371 Date: Mar. 15, 1999

§ 102(e) Date: Mar. 15, 1999

(87) PCT Pub. No.: WO97/47636

PCT Pub. Date: Dec. 18, 1997

(30) Foreign Application Priority Data

Jun. 13, 1996 (GB) .................................................. 9612600

(51) Int. Cl.[7] .............................. C07H 19/20; C07H 21/00
(52) U.S. Cl. ..................................... 536/25.34; 536/26.71; 536/26.72; 536/26.73; 536/26.74; 536/26.8
(58) Field of Search ............................... 536/25.34, 26.71, 536/26.72, 26.73, 26.74, 26.8

(56) References Cited

U.S. PATENT DOCUMENTS

| 4,689,407 |   | 8/1987  | Morr et al. . |
| 5,386,023 | * | 1/1995  | Sanghvi et al. . |
| 5,466,677 | * | 11/1995 | Baxter et al. . |
| 5,519,126 | * | 5/1996  | Hecht . |
| 5,658,731 | * | 8/1997  | Sproat et al. . |

FOREIGN PATENT DOCUMENTS

| 0121112   | 10/1984 | (EP) . |
| 0614907   | 9/1994  | (EP) . |
| 0629633   | 12/1994 | (EP) . |
| WO 9115499 | 10/1991 | (WO) . |
| WO 9220822 | 11/1992 | (WO) . |
| WO 9220823 | 11/1993 | (WO) . |
| WO 96/08503 | 3/1996 | (WO) . |

OTHER PUBLICATIONS

Lo A. et al., J. of Pharmaceutical Sciences, vol. 64(10), "Analysis of N–Glycosyl Bond Length in Crystal Structures of Nucleosides and Nucleotides," pp. 1707–1710 (1975).

* cited by examiner

Primary Examiner—James O. Wilson
(74) Attorney, Agent, or Firm—Woodcock Washburn LLP

(57) ABSTRACT

A compound of formula (I) wherein $B^1$ is a radical of a nucleoside base, $R^1$ is hydrogen or a hydroxy-protecting group, $R^2$ is hydrogen, hydroxy or a 2'-nucleoside-modifying atom or group, $R^3$ is an unsubstituted or substituted $C_1$ to $C_{10}$ alkyl, $C_2$ to $C_{10}$ alkenyl, $C_4$ to $C_{10}$ cycloalkylalkyl, $C_6$ to $C_{10}$ aryl or $C_7$ to $C_{13}$ aralkyl group, and Z is halogen or a group of formula (II) where $R^4$ and $R^5$ are each independently an unsubstituted or substituted $C_1$ to $C_{10}$ alkyl, $C_2$ to $C_{10}$ alkenyl, $C_4$ to $C_{10}$ cycloalkylalkyl, $C_6$ to $C_{10}$ aryl or $C_7$ to $C_{13}$ aralkyl group, or $R^4$ is said group and $R^5$ is hydrogen or $R^4$ and $R^5$ together with the nitrogen atom to which they are attached denote a five- to thirteen-membered heterocyclic ring, or Z is a group of formula (III): Nuc-O—, where Nuc is the residue of a natural or synthetic nucleoside or oligonucleotide after removal of a 5'-hydroxyl group therefrom attached through a 5'-methylene thereof to the indicated oxygen atom.

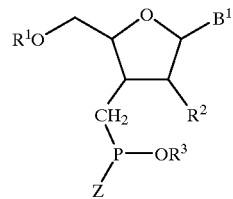

I

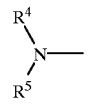

II

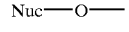

III

24 Claims, No Drawings

INTERMEDIATES FOR OLIGONUCLEOTIDE SYNTHESIS

This invention relates to chemical compounds which are intermediates for oligonucleotides and the use of such compounds in the preparation of oligonucleotides.

Accordingly, the present invention provides, in one aspect, a compound of formula

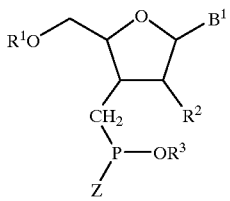

I where $B^1$ is a radical of a nucleoside base, $R^1$ is hydrogen or a hydroxy-protecting group, $R^2$ is hydrogen, hydroxy or a 2' nucleoside-modifying atom or group, $R^3$ is an unsubstituted or substituted $C_1$ to $C_{10}$ alkyl, $C_2$ to $C_{10}$ alkenyl, $C_4$ to $C_{10}$ cycloalkylalkyl, $C_6$ to $C_{10}$ aryl or $C_7$ to $C_{13}$ aralkyl group, and Z is halogen or a group of formula

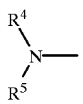

II where $R^4$ and $R^5$ are each independently an unsubstituted or substituted $C_1$ to $C_{10}$ alkyl, $C_2$ to $C_{10}$ alkenyl, $C_4$ to $C_{10}$ cycloalkylalkyl, $C_6$ to $C_{10}$ aryl or $C_7$ to $C_{13}$ aralkyl group, or $R^4$ is said group and $R^5$ is hydrogen, or $R^4$ and $R^5$ together with the nitrogen atom to which they are attached denote a five- to thirteen- membered heterocyclic ring; or Z is a group of formula

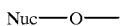

III where Nuc is the residue of a natural or synthetic nucleoside or oligonucleotide after removal of a 5' hydroxyl group therefrom attached through a 5' methylene thereof to the indicated oxygen atom.

When $R^3$, $R^4$ or $R^5$ denote a substituted alkyl, alkenyl, cycloalkylalkyl, aryl or aralkyl group, the group is preferably substituted by halogen, hydroxy, $C_1$–$C_4$ alkoxy, cyano, nitro or tri($C_1$–$C_{15}$ hydrocarbyl)silyl or, in the case of $R^3$, by $C_1$–$C_4$ alkylsulphonyl or $C_6$–$C_{10}$ arylsulphonyl.

When a tri($C_1$–$C_{15}$ hydrocarbyl)silyl group is present in compounds of formula I, it may be, for example, trialkylsilyl such as trimethylsilyl, triethysilyl, tri-n-propylsilyl, tri-isopropylsilyl, tri-n-butylsilyl, tri-isobutysilyl, isopropyldimethylsilyl, ter.butyldimethylsilyl or 1,1,2,2-tetramethylethyldimethylsilyl (thexyldimethylsilyl), triarylsilyl such as triphenylsilyl, triarylalkylsilyl such as tribenzylsilyl, aryldialkylsilyl such as phenyldimethylsilyl, phenyldiethylsilyl, phenyldiisopropylsilyl or phenyl di-tert-butylsilyl, or alkyldiarylsilyl such as methyldiphenylsilyl, isopropyldiphenylsilyl or tert-butyldiphenylsilyl. Where $R^3$, $R^4$ or $R^5$ has a tri($C_1$–$C_{15}$ hydrocarbyl)silyl substituent, it is preferably tri($C_1$–$C_4$ hydrocarbyl)silyl, especially trimethylsilyl. $R^1$ as tri($C_1$–$C_{15}$ hydrocarbyl)silyl is preferably $C_1$–$C_6$ alkyldi($C_6$–$C_8$ aryl)silyl, especially tert-butyldiphenylsilyl, or branched $C_2$–$C_4$ alkyl di ($C_1$–$C_4$ alkyl)silyl, especially thexyldimethylsilyl.

$R^1$ may be any hydroxy-protecting group capable of protecting a 5'-hydroxyl group against undesired reaction. Such groups are well known and include $C_1$ to $C_{10}$ aliphatic, e.g. alkyl groups; $C_3$ to $C_8$ cycloaliphatic, e.g. cycloalkyl, groups; $C_6$ to $C_{10}$ aromatic, e.g. aryl, groups; $C_7$ to $C_{40}$ araliphatic, e.g. aralkyl or $C_1$ to $C_4$-alkoxy-substituted aralkyl groups; groups of formula —COR or —SO$_2$R where R is a $C_1$ to $C_{10}$ aliphatic group, a $C_3$ to $C_8$ cycloaliphatic group, a $C_6$ to $C_{10}$ aromatic group or a $C_7$ to $C_{40}$ araliphatic group; and tri($C_1$–$C_{15}$ hydrocarbyl)silyl groups. Preferably $R^1$ is hydrogen or a 5'-protecting group conventionally used in oligonucleotide synthesis, more preferably hydrogen, a $C_7$ to $C_{40}$ araliphatic group or a tri($C_1$–$C_{15}$ hydrocarbyl)silyl group, especially an unsubstituted or substituted triphenylmethyl group such as methoxytrityl, dimethoxytrityl or tris tert-butyltrityl or a $C_1$–$C_6$ alkyldi($C_6$–$C_8$ aryl)silyl group such as tert-butyldiphenylsilyl, particularly dimethoxytrityl or tert-butyldiphenylsilyl.

$R^2$, the 2' nucleoside-modifying atom or group, i.e. an atom or group which may be attached to the 2' position of a nucleoside in place of a hydrogen atom or hydroxy group to effect a modification, may be a halogen atom such as a fluorine, chlorine or bromine atom; $C_1$ to $C_{10}$ unsubstituted alkyl, such as methyl, trifluoromethyl, ethyl, propyl, butyl, pentyl, hexyl, octyl or decyl; $C_6$ to $C_{10}$ aryl such as phenyl, tolyl or xylyl; $C_7$ to $C_{13}$ aralkyl such as benzyl; amino, $C_1$ to $C_{10}$ alkyl amino such as methylamino, ethylamino or octylamino; $C_1$ to $C_{10}$ alkylthio such as methylthio, ethylthio or octylthio; azide; nitrate; nitrite; cyanide; cyanate; methanesulphonate; $C_1$ to $C_{10}$ aminoalkylamino; a group of formula —OR$^6$ or —OCOR$^6$ where R$^6$ is a $C_1$ to $C_{30}$ organic group; substituted silyl; an RNA cleaving group; a cholesteryl group; a conjugate; a reporter group; an intercalator, a group for improving the pharmacokinetic properties of an oligonucleotide; or a group for improving the pharmacodynamic properties of an oligonucleotide.

Preferably $R^2$ is hydrogen, halogen, hydroxy or a group of formula —OR$^6$ or —OCOR$^6$ where R$^6$ is a $C_1$ to $C_{10}$ alkyl group such as methyl, ethyl, n-propyl, isopropyl, n-butyl, tert-butyl, n-pentyl, isopentyl, n-hexyl, n-heptyl, r-octyl, 2-ethylhexyl, n-nonyl or n-decyl, $C_2$ to $C_{10}$ alkenyl group such as vinyl, allyl, methallyl, butenyl, pentenyl, hexenyl, heptenyl, octenyl, nonenyl or decenyl, a $C_3$ to $C_8$ cycloalkyl group such as cyclopropyl, cyclobutyl, cyclopentyl, cyclohexyl, methylcyclopentyl, cyclohexyl, methylcyclohexyl, cycloheptyl or cyclooctyl, a $C_4$ to $C_{10}$ cycloalkylalkyl group such as cyclopropylmethyl, cyclobutylmethyl, cyclohexylmethyl, methylcyclohexylmethyl, cyclohexyl ethyl or dimethyl cyclohexylethyl, a $C_6$ to $C_{10}$ aryl group such as phenyl, ortho-, meta- or para-tolyl, ortho-, meta- or para-xylyl or naphthyl or a $C_7$ to $C_{25}$ aralkyl group such as benzyl, phenylethyl, diphenylmethyl or triphenylmethyl, any of which groups may be unsubstituted or substituted, for example by halogen, hydroxy, $C_1$ to $C_4$ alkoxy or cyano, or, where $R^2$ is of formula —OR$^6$, $R^6$ is a tri($C_1$–$C_{15}$ hydrocarbyl)silyl group.

In more preferred embodiments, $R^2$ is hydrogen, hydroxy, fluorine, a group of formula —OR$^6$ where R$^6$ is a $C_1$ to $C_4$ alkyl group, a $C_2$ to $C_4$ alkenyl group, a $C_7$ to $C_{13}$ aralkyl group or a group of formula —(R$^7$—O)$_n$—R$^8$ where R$^7$ is $C_1$ to $C_4$ alkylene, R$^8$ is $C_1$ to $C_4$ alkyl and n is 1 to 8, or R$^2$ is a group of formula —OCOR$^6$ where R$^6$ is $C_1$ to $C_4$ alkyl or $C_6$ to $C_8$ aryl. In especially preferred embodiments, $R^2$ is hydrogen, hydroxy, fluorine, methoxy, ethoxy, allyloxy, benzyloxy, methoxyethoxy, —O(CH$_2$—CH$_2$—O—)$_3$—CH$_3$, acetoxy or benzoyloxy.

$R^3$, $R^4$ or $R^5$ as $C_1$ to $C_{10}$ alkyl may be, for example a straight or branched group such as methyl, ethyl, n-propyl, isopropyl, r-butyl, isobutyl, tert-butyl, n-pentyl, isopentyl, n-hexyl, n-heptyl, n-octyl, 2-ethylhexyl, n-nonyl or n-decyl. $R^3$, $R^4$ or $R^5$ as $C_2$ to $C_{10}$ alkenyl may be, for example, vinyl, allyl, methallyl, butenyl, pentenyl, hexenyl, heptenyl, octenyl, nonenyl or decenyl. $R^3$, $R^4$ or $R^5$ as $C_4$ to $C_{10}$ cycloalkylalkyl may be, for example, cyclopropylmethyl, cyclobutylmethyl, cyclopentylmethyl, cyclopentylethyl, methylcyclopentylmethyl, cyclohexylmethyl, cyclohexylethyl, methylcyclohexylmethyl, methylcyclohexylethyl, dimethylcyclohexylmethyl or dimethylcyclohexylethyl. $R^3$, $R^4$ or $R^5$ as $C_6$ to $C_{10}$ aryl may be, for example, phenyl, o-tolyl, m-tolyl, p-tolyl, o-xylyl, m-xylyl or p-xylyl. $R^3$, $R^4$ or $R^5$ as $C_7$ to $C_{13}$ aralkyl may be, for example, benzyl, phenylethyl or diphenylmethyl. Any of the above groups as $R^3$, $R^4$ or $R^5$ may be unsubstituted or substituted as hereinbefore described.

When $R^4$ and $R^5$ together with the attached nitrogen atom denote a heterocyclic ring, this ring may be, for example, a five-membered ring such as a pyrrolidine ring, a six-membered ring such as a piperidine, 2,6-dimethylpiperidine, N-methylpiperazine, morpholine or thiomorpholine ring, a seven-membered ring such as a perhydroazepine ring, an eight-membered ring such as a perhydroazocine ring, a nine-membered ring such as perhydroazonine ring, a ten-membered ring such as a perhydroazecine ring, an eleven-membered ring such as an azacycloundecane ring, a twelve-membered ring such as an azacyclododecane ring or a thirteen-membered ring such as an azacyclotridecane ring.

$R^3$ is preferably unsubstituted or substituted $C_1$ to $C_4$ alkyl, $C_3$ to $C_5$ alkenyl, $C_6$ to $C_8$ cycloalkylalkyl or $C_7$ to $C_9$ aralkyl, especially methyl, ethyl, 2-cyanoethyl, 2,2,2-trichloroethyl, allyl, benzyl or 2-(trimethylsilyl)ethyl.

When Z in formula I is a group of formula II, in preferred embodiments $R^4$ and $R^5$ independently are unsubstituted or substituted $C_1$ to $C_4$ alkyl, $C_3$ to $C_5$ alkenyl, $C_6$ to $C_8$ cycloalkylalkyl or $C_7$ to $C_9$ aralkyl, or $R^4$ is $C_1$ to $C_4$ alkyl, preferably branched $C_1$ to $C_4$ alkyl such as isopropyl or tert-butyl, or $C_7$ to $C_9$ aralkyl such as benzyl, and $R^5$ is hydrogen, or $R^4$ and $R^5$ together with the attached nitrogen atom denote a five- or six-membered heterocyclic ring having one or two heteroatoms in the ring. In especially preferred embodiments, $R^4$ and $R^5$ are independently methyl, ethyl, n-propyl, isopropyl, n-butyl, sec-butyl, isobutyl, tert-butyl, allyl or benzyl, or $R^4$ and $R^5$ together with the attached nitrogen atom denote a pyrrolidine, piperidine or morpholine ring.

When Z in formula I is a group of formula III, the residue Nuc may be the residue, after removal of a 5'hydroxyl group, of any natural or synthetic nucleoside, for example adenosine, cytidine, guanosine, thymidine, uridine, 2-aminoadenosine, 6-N-benzyladenosine, 5-N-methylcytidine, 4-N-benzoylcytidine, 5-propynylcytidine, 2-N-isobutyrylguanosine, N-benzyloxymethylthymidine or 5-fluorouracil, or an oligonucleotide derived therefrom which may be a dinucleotide, trinucleotide or higher oligomer, and which may have natural, i.e. phosphodiester, intemucleoside linkages or synthetic analogues thereof such as phosphorothioate or methylphosphonate linkages, or P (III) precursors of such intemucleoside linkages.

$B^1$ in formula I may be a radical of a base found in naturally occurring nucleosides, which may be unsubstituted or substituted, for example on a nitrogen atom by a protecting group, e.g. an acyl group, which may be aliphatic such as acetyl, or aromatic such as benzoyl or nitrobenzoyl, or by an aralkyloxyalkyl protecting group such as benzyloxymethyl, or synthetic analogues of such bases. Other types of protecting group conventionally used in nucleotide chemistry which may be present on a nitrogen atom in $B^1$ include amidine groups, such as N, N-dimethyl formamidine, N,N-dimethylacetamidine and N-methylpyrrolidine amidine groups, and alkoxy carbonyl groups such as tert-butoxy carbonyl which convert an amino group into a carbamate group.

Thus $B^1$ may be a radical of a purine or pyrimidine base such as adenine, guanine, cytosine, thymine or uracil, or an analogue of these bases such as 2-aminoadenine, 6-hydroxypurine, 5-methylcytosine, 5-propynylcytosine, 5-fluorouracil, 5-propynyluracil or dihydrouracil, or such a radical substituted on a nitrogen atom, for example by a protecting group as hereinbefore described.

In certain preferred embodiments where Z is a group of formula III, Nuc is a residue of a nucleoside or oligonucleotide as hereinbefore described attached at a terminal 3' position to a solid support such as a support used in solid phase oligonucleotide synthesis, for example to an inert silica-based support, such as controlled pore glass (CPG), containing long chain alkylamino groups, by a linker such as a succinyl group. The solid support may also contain groups to act as 3' terminal modifying groups for an oligonucleotide to be synthesised on the support.

Compounds of the invention may be in the form of one of the possible isomers, for example as a diastereoisomer, an optical isomer, a racemate or a mixture thereof. Preferred isomers of compounds of formula I are those of formula

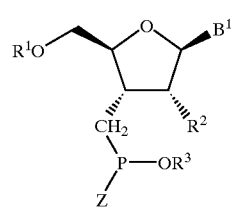

IV where $B^1$, $R^1$, $R^2$ and $R^3$ are as hereinbefore defined.

Specific especially preferred compounds of formula I are those hereinafter described in the Examples.

Compounds of formula I where Z is a group of formula II may be prepared by reacting a compound of formula I where Z is halogen, i.e. a compound of formula

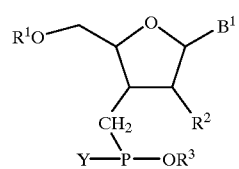

V where $B^1$, $B^1$, $R^2$ and $R^3$ are as hereinbefore defined and Y is halogen, with a compound of formula

VI where $R^4$ and $R^5$ are as hereinbefore defined. The reaction may be carried out in an organic solvent, for example a halogenated hydrocarbon such as chloroform, in the presence of a tertiary nitrogen base such as pyridine, and at a temperature from −78° C. to 50° C., preferably from −30° C. to 25° C.

Compounds of formula V may be prepared by non-oxidative halogenation of a compound of formula

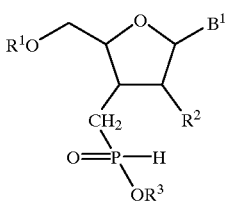

VII where $B^1$, $R^1$, $R^2$ and $R^3$ are as hereinbefore defined. Non-oxidative halogenation may be carried out by reacting the compound of formula VII with a non-oxidative halogenating agent, for example a halophosphorane such as triphenyldichlorophosphorane or dichloro tris (2,4,6-tribromophenoxy)phosphorane in the presence of a base, preferably a tertiary nitrogen base such as pyridine, in an organic solvent, which may be pyridine but is preferably a halohydrocarbon such as chloroform, at a temperature from −20° C. to 60° C., preferably from 0° C. to 50° C.

Compounds of formula VI are amines which are commercially available or may be prepared by known procedures.

Compounds of formula VII and their preparation are described in WO 96/08503.

Compounds of formula I where Z is a group of formula III may be prepared by reacting a compound of formula I where $R^1$ is a hydroxy-protecting group and Z is a group of formula II with a natural or synthetic nucleoside or oligonucleotide having a free 5' hydroxyl group (including oligonucleotides having one or more P(III) precursor internucleoside linkages). The reaction may be carried out in solution or with the nucleoside or oligonucleotide attached to a solid carrier, as hereinbefore described. It has been found that the reaction may be carried out under conditions, and using procedures, known for coupling reactions between a nucleoside having a 3' phosphoramidite group and a nucleoside or oligonucleotide having a free 5'hydroxyl group in conventional oligonucleotide synthesis—see, for example 'Oligonucleotides and Analogues, A Practical Approach' ed. F. Eckstein, IRL Press 1991.

Thus the compound of formula I where Z is a group of formula II may be reacted with the nucleoside or oligonucleotide in the presence of an amine-protonating coupling catalyst (activating agent) such as tetrazole or 5-(4-nitrophenyl)tetrazole to give a compound of formula I where Z is a group of formula III. The reaction may be carried out at −20 to 50° C., preferably at room temperature.

When the compound of formula I where Z is a group of formula III is reacted with a nucleoside or oligonucleotide attached to a solid support the product is a compound of formula I in which Z is a group of formula III where Nuc is a residue of a nucleoside or oligonucleotide attached to a solid support.

Compounds of formula I where Z is a group of formula III are intermediates for the preparation of oligonucleotides having more nucleoside units than an oligonucleotide residue in Nuc. Accordingly, the present invention also provides a method of preparing an oligonucleotide of formula

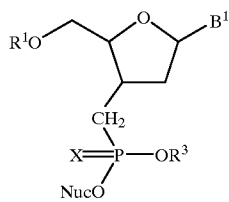

VIII where $B^1$, $R^1$, $R^3$ and Nuc are as hereinbefore defined and X is oxygen or sulphur, which comprises subjecting a compound of formula I where Z is a group of formula III to oxidation to form an oligonucleotide of formula VIII where X is oxygen or to sulphurisation to give an oligonucleotide of formula VII where X is sulphur.

It has been found that oxidation or sulphurisation of compounds of formula I where Z is a group of formula III may be effected by methods used for oxidation or sulphurisation respectively of phosphite internucleoside linkages. Thus oxidation of compounds of formula I where Z is a group of formula III may be effected by treatment with iodine and water, or with a hydroperoxide such as tert-butyl hydroperoxide, for example using conditions and procedures known for oxidation of phosphite internucleoside linkages in oligonucleotide synthesis. Sulphurisation of compounds of formula I where Z is a group of formula III may be effected by treatment with sulphur in the presence of a tertiary amine in an organic solvent, usually carbon disulphide, by treatment with [3H] 1,2-benzodithiol-3-one-1,1-dioxide (Beaucage reagent) or by treatment with tetraethylthiuram, for example using procedures known for sulphurisation of phosphite internucleoside linkages. Both oxidation and sulphurisation are generally carried out at room temperature.

Accordingly, the invention provides in another aspect a method of preparing an oligonucleotide which comprises subjecting a nucleoside having a protected 5' hydroxy group and, at the 3' position, a group of formula

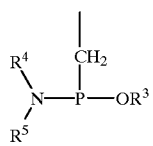

IX where $R^3$, $R^4$ and $R^5$ are as hereinbefore defined, to a nucleoside coupling reaction with a natural or synthetic nucleoside or oligonucleotide having a free 5' hydroxy group, to form an oligonucleotide precursor having an internucleoside linkage of formula

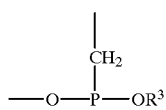

where $R^3$ is as hereinbefore defined, and converting the precursor into an oligonucleotide having an internucleoside linkage of formula

XI

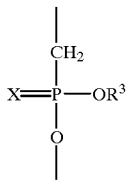

where $R^3$ is as hereinbefore defined and X is oxygen or sulphur by oxidising the precursor to give an oligonucleotide having an internucleoside linkage of formula XI where X is oxygen or sulphurising the precursor to give an oligonucleotide having an internucleoside linkage of formula XI where X is sulphur.

The nucleoside having at the 3' position a group of formula IX, the nucleoside or oligonucleotide having a free 5' hydroxy group and the methods of carrying out the reactions may be as hereinbefore described.

Oligonucleotides of formula VIII where Nuc is a residue of a nucleoside or oligonucleotide attached to a solid support may be treated to remove the 5' protecting group $R^1$ and the resulting 5' hydroxy-terminated oligonucleotide subjected to successive coupling reactions with a natural or synthetic nucleoside or oligonucleotide having a protected 5' hydroxyl group and, at the 3' position, a group reactive with, or activatable to be reactive with, the free 5' hydroxy group on the deprotected oligonucleotide of formula VIII attached to the solid support, until an oligonucleotide of the desired length is obtained. Thus the oligonucleotide of formula VIII may be coupled with a nucleoside or oligonucleotide having a 3' phosphoramidite, H-phosphonate or phosphodiester group and a protected 5' hydroxyl group, or with a compound of formula I where Z is a group of formula II, to give a chain-extended oligonucleotide which may in turn be further chain extended by further such alternative reactions until an oligonucleotide of the desired length is obtained. Where a nucleoside or oligonucleotide having a 3' phosphoramidite, H-phosphonate or phosphodiester group is used, the coupling reactions may be carried out using procedures known in oligonucleotide synthesis. Where a compound of formula I where Z is a group of formula II is used, the coupling reaction may be carried out as hereinbefore described. Thus, where a 3' phosphoramidite or a compound of formula I where Z is a group of formula II is used, a coupling cycle involves an oxidation or sulphurisation step, while where a 3' H-phosphonate is used oxidation or sulphurisation is effected after chain extension is complete, and where a 3' phosphodiester is used no oxidation is required.

When an oligonucleotide having the desired number of nucleosides has been synthesised, it may be treated to remove hydroxy-protecting groups such as dimethoxytrityl groups, using conventional methods, for example by treatment with an aqueous organic acid such as trifluoroacetic acid. Where the oligonucleotide has been synthesised on a solid support, this treatment may be effected before or after detachment of the oligonucleotide from the support, for example using conventional methods such as treatment with concentrated aqueous ammonia, which treatment also removes a protecting group which may have been present on an exocyclic nitrogen atom in one or more of the nucleosides used in the synthesis of the oligonucleotide. The terminal 5' hydroxyl generated on deprotection can be reacted to introduce a 5' terminal modifying group, such as a phosphate group or other 5' modifying group, for example using the procedures described by Beaucage and Iyer, Tetrahedron 49, 1925–63 (1993).

The invention is illustrated by the following Examples.

In the formulae of compounds of the Examples and their precursors, Et is ethyl, Me is methyl, T is 1-thyminyl, t-Bu is tert-butyl, Ph is phenyl and DMTr is dimethoxytrityl.

Compounds used in the Examples and precursors thereof are prepared as follows:

Compound A

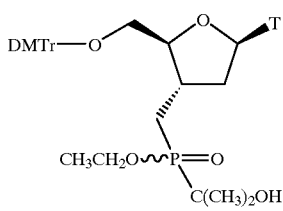

This is Compound 87 of WO 96/08503, prepared as described in Example 84 of WO 96/08503.

Compound B

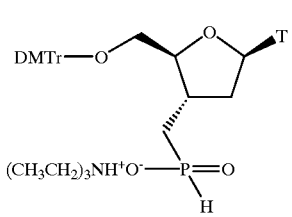

To a solution of Compound A (0.85 g, 1.22 mmol) in anhydrous methanol (10 ml) is added sodium methoxide (1.5 ml 4.4N solution in methanol). After stirring for 16 hours at room temperature, concentration and purification by flash silica column chromatography (gradient elution-chloroform, methanol, triethylamine 100:20:1–100:35:1), followed by further purification by passing a solution of the product in aqueous 0.5% triethylamine through a Dowex 50W-X2 ion exchange column (triethylamine form) gives, after concentration, Compound B.

$^{31}P$ nmr $^1H$ decoupled ($CD_3OD$, 162 MHz) $\delta$23.7 ppm.

Compound C

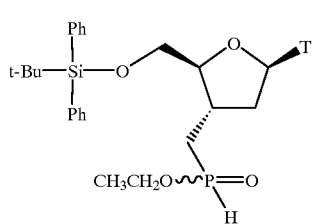

This is Compound 84 of WO 96/08503, prepared as described in Example 81 of WO 96/08503.

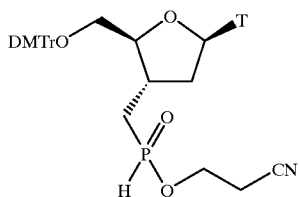

Compound D

To a solution of Compound B (500 mg, 0.71 mmol) and dicyclohexylcarbodiimide (189 mg, 0.92 mmol) in dry THF (5.4 ml) under argon at room temperature is added 3-hydroxy propionitrile (58 μl, 0.85 mmol). The resulting solution is heated at 55° C. for 2 hours. After cooling the mixture is filtered and diluted with ethyl acetate (20 ml) and washed with water and brine, dried over $Na_2SO_4$, filtered and concentrated. The resulting product is taken up in dichloromethane (5 ml) and filtered and concentrated, this process being repeated as required to remove dicycdohexyl urea, to give Compound D, isolated as a mixture of diastereoisomers at phosphorus.

Alternative Method: To solution of Compound B (123 g, 17.4 mmol) and dicyclohexylcarbodiimide (3.94 g, 19.1 mmol) in THF (120 ml) under argon is added 3-hydroxypropionitrile (1.42 ml, 20.8 mmol) and the resulting mixture is heated to 60° C. for 4 hours. Concentration to approximately half volume is followed by dilution with an equivalent volume of ethyl acetate and filtration to remove the resultant percipitate. The organic phase, which after washings of the filtrate with ethyl acetate is now approximately 200 ml, is washed with water (4×80 ml) and saturated brine (6×80 ml), dried over sodium sulphate and concentrated. The resulting solid is redissolved in acetonitrile (200 ml) and extracted with hexane (6×50 ml). The acetonitrile phase is then concentrated and dried under high vacuum to give Compound D.

Found C 62.2%; H 5.9%; N 6.5%

$C_{35}H_{38}N_3O_8P.H_2O$ requires C 62.05%; H 5.95%; N 6.2%

$^{31}P$ nmr $^1H$ decoupled (162 MHz, $CDCl_3$) δ37.5, 37.3 ppm.

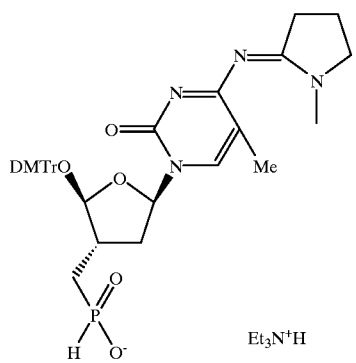

Compound E

This is Compound 100 of WO 96/08503, prepared as described in Example 98 of WO 96/08503.

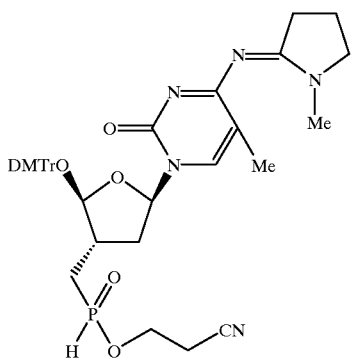

Compound F

To a solution of Compound E (0.47 g, 0.60 mmol) dicyclohexylcarbodiimide (DCC) (0.148 g, 0.72 mmol) and triethylamine hydrochloride (0.24 g, 1.8 mmol) in anhydrous chloroform (3 ml) under argon is added 3-hydroxypropionitrile (81 μl, 1.2 mmol). The resulting solution is heated at 60° C. for four hours. The mixture is then concentrated under vacuum, taken up in ethyl acetate (50 ml) and filtered. The resulting clear solution is extracted with water (3×20 ml) and saturated brine (8×20 ml). Drying over sodium sulphate, filtration and concentration under reduced pressure gives crude product containing DCC. The DCC is removed by dissolution of this crude product in acetonitrile and repetitative extraction with hexane.

Found C 63.35, H 6.50, N 8.80%;

$C_{40}H_{46}N_5O_7P.H_2O$ requires C 63.40, H 6.40, N 9.25%.

$^{31}P$ nmr $^1H$ decoupled (162 MHz, $CDCl_3$) δ38.1, 37.4 ppm.

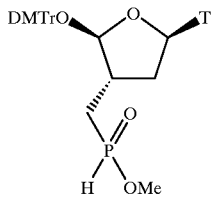

Compound G

To a solution of Compound B (1.0 g, 1.41 mmol) in dichloromethane (15 ml) under an argon atmosphere at 5° C. is added triethylamine (98 μl, 0.71 mmol) followed by the dropwise addition of methylchloroformate (142 μl, 1.84 mmol). After 5 minutes the solution is allowed to warm to room temperature, and is stirred for 45 minutes. The mixture is diluted with $CH_2Cl_2$ and washed with water, dried ($Na_2SO_4$) and concentrated. Purification by flash silica column chromatography (eluent ethylacetate:methanol 10:1) gives Compound G as a mixture of diastereomers at phosphorus.

$^{31}P$ nmr $^1H$ decoupled ($CDCl_3$, 162 MHz) δ37.3 and 37.0 ppm. $^1H$ nmr ($CDCl_3$, 500 MHz) δ8.10 (1H, brs, NH), 7.55 (1H, s, H6), 7.35 (2H, d, ArH), 7.25 (6H, m, ArH), 7.15 (1H, m, ArH), 7.00 (1H, d, P$\underline{H}$, J 530 Hz), 6.80 (4H, d, ArH), 3.75 (1H, m, H4'), 3.70 (6H, s, ArO$\underline{CH}_3$), 3.55 (1H, dd, H5'), 3.25 (1H, dd, H5'), 2.70 (1H, m, H3'), 2.45 (1H, m, H2'), 2.20 (1H, m, H2'), 1.75 (1H, m, H6'), 1.60 (1H, m, H6'), 1.45 (3H, brs, TC$\underline{H}_3$) ppm.

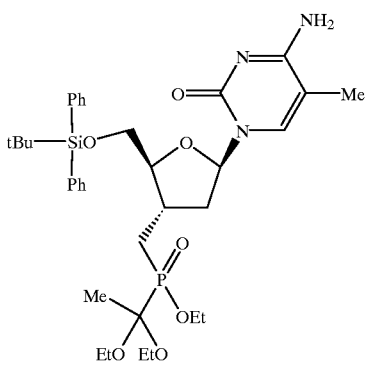

Compound H

Triazole (20.7 g, 0.3 mol) is carefully dried by coevaporation with dry pyridine (4×50 ml), then dissolved in pyridine (80 ml) and cooled to 0° C. under argon. Triethylamine (41.8 ml, 0.3 mol) is added and the mixture stirred during the addition of phosphorus oxychloride (6.87 ml, 75 mmol). The resulting solution is stirred at 0° C. for 15 minutes. A solution of carefully dried (coevaporation 3×50 ml pyridine) Compound 83 of WO 96/08503, prepared as described in Example 80 of WO 96/08503 (20.6 g, 30 mmol) in pyridine (50 ml) is added dropwise. The resulting strongly coloured solution is allowed to warm to room temperature. After 18 hours, the mixture is concentrated and dissolved in THF- (300 ml). Concentrated ammonia is added (90 ml) and the mixture is stirred at room temperature for 18 hours. Concentration and purification by flash silica column chromatography (gradient elution ethyl acetate plus methanol 10%–25%) gives Compound H as a mixture of diastereoisomers at phosphorus.

$^{31}$P nmr $^1$H decoupled (CD$_3$OD, 162 MHz) δ50.0 and 49.5 ppm.

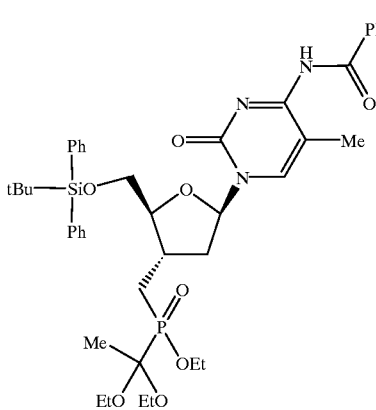

Compound J

To a solution of Compound H (7.87 g, 11.5 mmol) in dry THF (110 ml) under argon is added triethylamine (6.4 ml, 45.9 mmol) and the resulting solution cooled to −70° C. during the addition of benzoyl chloride (2.00 ml, 17.21 mmol). The solution is then allowed to warm to room temperature and is stirred overnight. The resulting mixture is partially concentrated, dissolved in ethyl acetate and washed twice with water and then once with brine. The solution is dried over Na$_2$SO$_4$, concentrated and purified by flash silica column chromatography (gradient elution hexane:ethyl acetate 1:5—pure ethyl acetate) to give Compound J as a mixture of 2 diastereoisomers at phosphorus.

$^{31}$P nmr $^1$H decoupled (CDCl$_3$, 162 MHz) δ47.0 and 46.8 ppm.

Found C 61.85, H 7.25, N 5.10%
C$_{42}$H$_{56}$O$_8$N$_3$PSi.3/2 H$_2$O requires C 61.75, H 7.30, N 5.15%

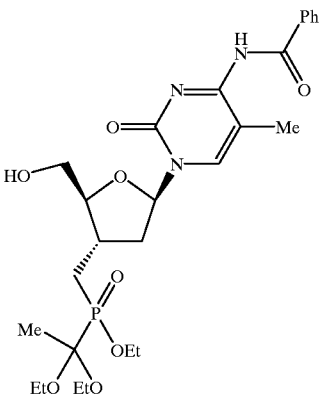

Compound K

To a solution of Compound J (14.5 g, 18.34 mmol) in dry THF (160 ml) is slowly added a solution of tetrabutylammonium fluoride in THF (20.2 ml, 20.2 mmol). The resulting solution is stirred at room temperature for 6 hours, evaporated to give a yellow oil and then purified by flash silica column chromatography (gradient elution ethyl acetate—ethyl acetate:ethanol 7:1) to give Compound K as a mixture of 2 diastereoisomers at phosphorus).

$^{31}$P nmr $^1$H decoupled (CDCl$_3$, 162 MHz) δ48.9 and 48.8 ppm.

Found C 55.65, H 7.00, N 7.35% C$_{26}$H$_{38}$O$_8$N$_3$P.½ H$_2$O requires C 55.70, H 7.00, N 7.50%

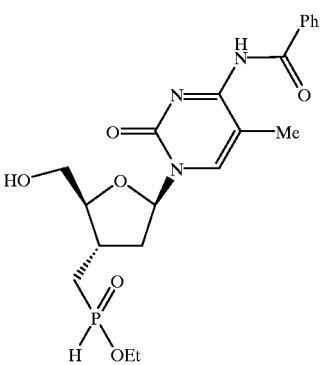

Compound L

Compound K (2.48 g, 4.50 mmol) is carefully dried by coevaporation from dry toluene (3×20 ml). Dichloromethane (45 ml) is added followed by ethanol (2.62 ml, 45 mmol), all under argon at room temperature. The resulting solution is stirred and cooled to −15° C. during the addition of trimethylsilyl chloride (5.69 ml, 45.0 mmol). The resulting mixture is thoroughly degassed with argon and slowly warmed to room temperature. After stirring at room temperature for 6 hours the mixture is diluted with dichloromethane and washed twice with sodium bicarbonate solution, dried over Na$_2$SO$_4$ and concentrated to give Compound L as a mixture of 2 diastereoisomers at phosphorus.

$^{31}$P nmr $^1$H decoupled (CDCl$_3$, 162 MHz) δ35.5 and 34.2 ppm.

Found C 55.5, H 6. 1 0, N 9.70% C$_{20}$H$_{26}$N$_3$O$_6$P requires C 55.15, H 6.00, N 9.65%

13

Compound M

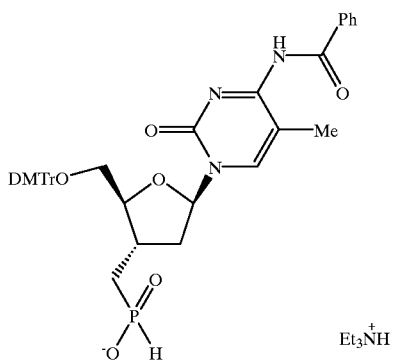

Compound L (4.79 g, 11.0 mmol) is carefully dried by coevaporation with dry pyridine (6×50 ml) and then dissolved in pyridine (80 ml) before addition of triethylamine (3.1 ml, 22 mmol) followed by dimethoxytrityl chloride (4.10 g, 12.1 mmol) at room temperature under argon. After 16 hours at room temperature the mixture is concentrated and stored at −20° C. overnight. The resulting solid is dissolved in THF (50 ml), triethylamine (15 ml) and water (10 ml) and stirred at room temperature for 7 hours. The resulting mixture is concentrated and purified by flash silica column chromatography (gradient elution ethyl acetate, triethylamine 50:1—ethyl acetate, methanol, triethylamine 55:45:2) to give Compound M.

$^{31}$P nmr $^1$H decoupled (CDCl$_3$, 202 MHz) δ22.4 ppm.

Found C 64.5, H 6.65, N 6.4% C$_{45}$H$_{55}$N$_4$O$_8$P.3/2H$_2$O requires C 64.5, H 6.95, N 6.7%

Compound N

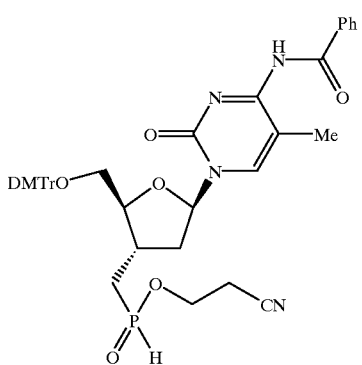

Compound N is prepared by the alternative method described for Compound D, but using Compound M as starting material in place of Compound B, and omitting acetonitrile-hexane partitioning.

$^{31}$P nmr $^1$H decoupled (CDCl$_3$, 162 MHz) δ37.2 and 36.8 ppm.

MS (FAB) M/Z 763 (MH$^+$).

14

EXAMPLE 1

Compound 1

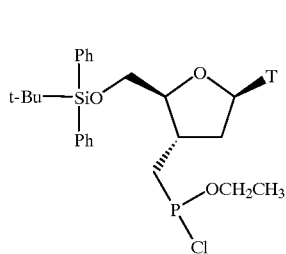

Compound 2

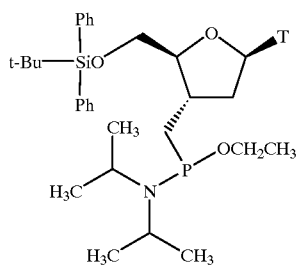

To a solution of carefully dried Compound C (40 mg, 70 μmol) in deuterochloroform (0.5 ml) containing pyridine (80 μl, 1 mmol) is added dichlorotriphenylphosphorane (113 mg, 350 μmol). The resulting mixture is shaken to dissolve the phosphorane and then allowed to stand at ambient temperature. The progress of the reaction is monitored by $^{31}$P nmr. The product, Compound 1, resonates at 201 ppm. After 16 hours, additional dichlorotriphenylphosphorane (45 mg, 140 μmol) is added. After an additional 24 hours, $^{31}$P nmr shows the reaction to be 95% complete. A total (150 μl, 1.07 mmol) of diisopropylamine is added in 30 μl portions to the crude reaction mixture at −30° C. The resulting mixture is allowed to warm to room temperature and then diluted with dichloromethane (20 ml), washed twice with deionised water (2×10 ml), dried (Na$_2$SO$_4$) and concentrated. Purification by flash silica column chromatography (gradient elution 4:1–2:1 hexane-ethylacetate) gives Compound 2 as a mixture of 2 diastereoisomers.

$^{31}$P nmr $^1$H decoupled (CDCl$_3$, 162 MHz) δ123.0, 122.3.

EXAMPLE 2

Compound 3

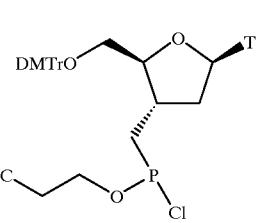

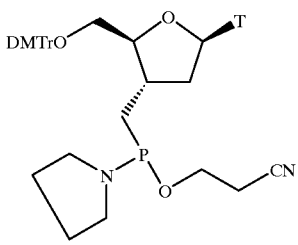

Compound 4

Using the procedure of Example 1, Compound D (30 mg, 44μmol) is converted firstly into Compound 3 and then, replacing the diisopropylamine used in Example 1 by pyrrolidine (56 μl, 0.67 mmol), into Compound 4.

EXAMPLE 3

Oligonucleotide 1, having the sequence 5'-TTT tTC TCT CTC TCT-3' where t represents a nucleoside unit derived from Compound 4, is prepared by standard solid phase phosphoramidite oligonucleotide synthesis as described in 'Oligonucleotides and Analogues A Practical Approach' ed. F. Eckstein, IRL Press 1991, except that Compound 4 is used instead of the usual 3'-phosphoramidite—substituted nucleoside at the appropriate point in the synthesis, so that a compound of formula I where Z is a group of formula III in which Nuc is a residue of the oligonucleotide TC TCT CTC TCT is formed and then oxidised to an oligonucleotide of formula VIII where X is oxygen in the standard oxidation step, this oligonucleotide being coupled further to give Oligonucleotide 1.

EXAMPLE 4

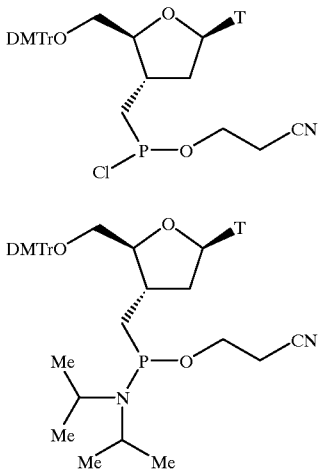

Compound 3

Compound 5

To a stirred solution of bis(trichloromethyl)carbonate (1.01 g, 3.40 mmol) in dry dichloromethane (10 ml) under an argon atmosphere at 5° C. is added a solution of triphenylphosphine (2.68 g, 10.21 mmol) in dry dichloromethane (8 ml +7 ml washings). The mixture is immediately allowed to warm to room temperature over 5 minutes, pyridine (1.24 ml) is then added and the mixture thoroughly mixed and recooled to 5° C. To the resulting pale brown solution is added a solution of Compound D (3.45 g, 5.11 mmol) in dry dichloromethane (10 ml+5 ml washings) containing pyridine (1.24 ml). On completion of addition the solution is allowed to warm to room temperature. After stirring at room temperature for 1 hour the mixture contains Compound 3 ($^{31}$P nmr δ206.7 ppm). The mixture is cooled to −30° C. and diisopropylamine (3.57 ml, 27 mmol) added over 5 minutes. The mixture is allowed to warm to room temperature over 10 minutes and then concentrated to half volume under vacuum. This solution is immediately transferred onto the top of a flash silica chromatography column (300 g, silica) eluting with hexane:tetrahydrofuran:triethylamine 25:25:1. Some pure product fractions result. Impure fractions are subjected to further chromatography on flash silica, eluting with hexane:tetrahydrofuran:dichloromethane:triethylamine 25:25:10:1. All product fractions are pooled and concentrated to give Compound 5 isolated as a white foam and as a mixture of diastereoisomers at phosphorus.

Found C 66.2; H 7.25, N 7.5%; $C_{41}H_{51}O_7N_4P$ requires C 66.3, H 6.9, N 7.55%.

$^{31}$P $^1$H decoupled (162 MHz, CDCl$_3$) δ128.3, 127.8 ppm. M/Z (ES$^+$) 743 (M+H)$^+$(ES) 741 (M−H )$^-$.

EXAMPLE 5

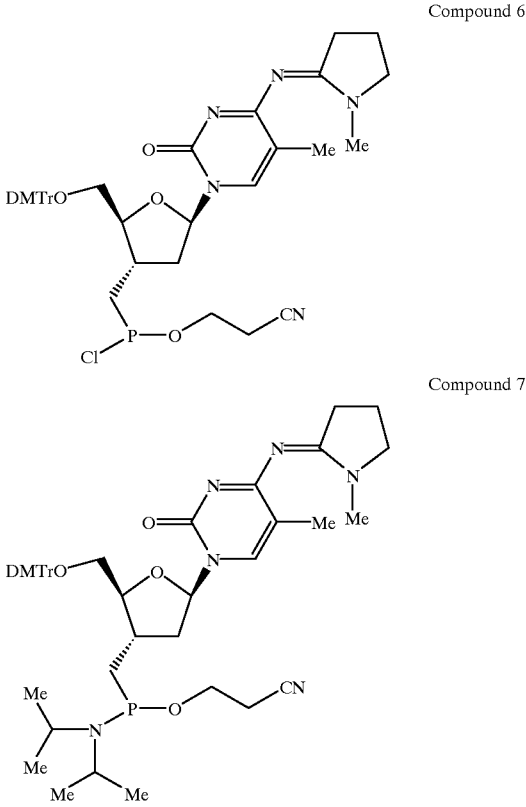

Compound 6

Compound 7

Compounds 6 and 7 are prepared by the method of Example 4 but substituting Compound F for Compound D. The reaction is carried out with the same mole quantities of reagents but at half the concentration. In the initial phase of the preparation the reaction is allowed to proceed for 2 hours rather than 1 hour to give Compound 6 ($^{31}$P nmr δ205.7 ppm). The final work up involves washing the crude product twice with water, concentration and purification by flash silica column chromatography (eluant ethyl acetate/methanol 10:1+2% Et$_3$N) to give Compound 7 as a mixture of 2 diastereomers.

Found C 63.85, H 7.05, N 9.55% C$_{46}$H$_{59}$N$_6$O$_6$P.2H$_2$O requires C 64.25, H 7.35, N 9.80%

$^{31}$P nmr $^1$H decoupled (CDCl$_3$, 162 MHz) δ128.6 and 128.1 ppm.

M/Z (ES$^+$)823 (MH$^+$).

EXAMPLE 6

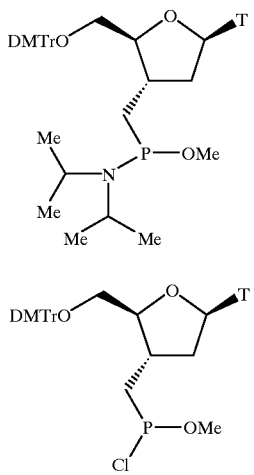

Compound 9

Compound 8

Compounds 8 and 9 are prepared by the method of Example 4 but substituting Compound G for Compound D. The initial phase of the reactions gives Compound 8 ($^{31}$P nmr 67 207.7 ppm). Final purification is performed by repetitative flash silica column chromatography, firstly eluting with (hexane/ethyl acetate 2:1+2% Et$_3$N) and subsequently with (hexane/diethyl ether 1:3+2% Et$_3$N) to give Compound 9 as a mixture of 2 diastereomers.

$^{31}$P nmr $^1$H decoupled (CDCl$_3$, 202 MHz) δ128.8 and 127.8 ppm.

MZ (ES$^+$) (704,705,706, MH$^+$) (ES) (702,703,704 M-H$^-$).

EXAMPLE 7

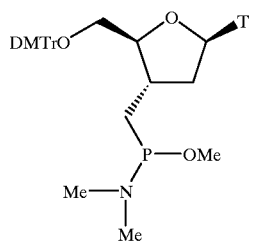

Compound 10

Compound 10 is prepared by the method of Example 6, but replacing the diisopropylamine used in Example 6 by dimethylamine, the intermediate Compound 8 being reacted with a 2.0 molar solution of dimethylamine in THF. Final purification by flash silica column chromatography (eluant ethyl acetate/hexane 3:1+2% Et$_3$N) gives Compound 10 as a mixture of 2 diastereomers.

$^{31}$P nmr $^1$H decoupled (CDCl$_3$, 162 MHz) δ144.3 and 144.2 ppm.

EXAMPLE 8

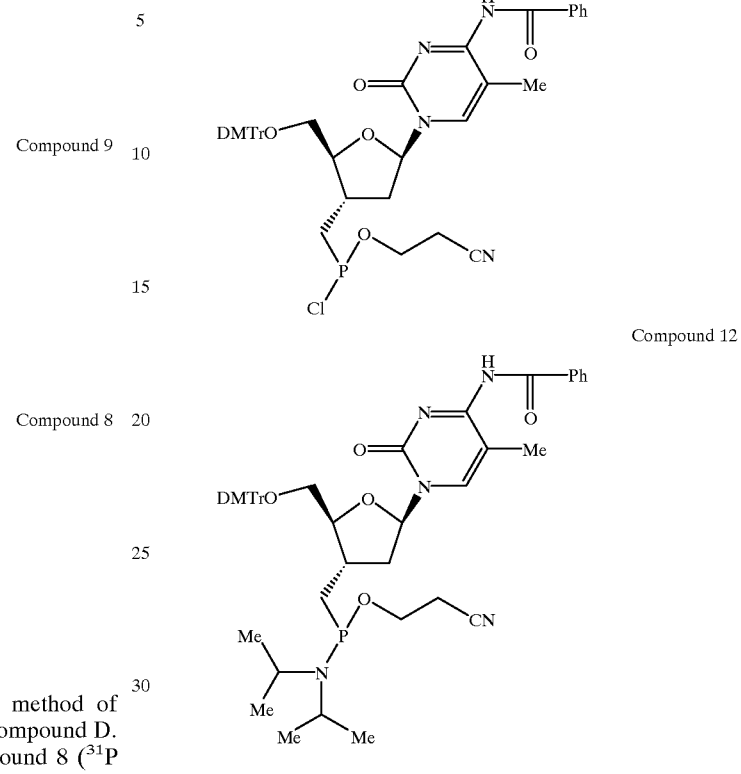

Compound 11

Compound 12

Compounds 11 and 12 are prepared by the method of Example 10, but substituting Compound N for Compound D. In this case the final product Compound 12 is purified by flash silica column chromatography (hexane-THF-triethylamine 50:50:1):

$^{31}$P nmr $^1$H decoupled (CDCl$_3$, 162 MHz) δ128.1 and 127.6 ppm.

MS (ES$^+$) 846, 847,848 (MH)$^+$(ES) 844, 845, 846 (M–H)$^-$

EXAMPLES 9–15

The following modified oligonucleotides are prepared by standard DNA synthesis technology using a phosphoramidite strategy. All couplings are performed as double couplings, that is after exposing the support bound oligonucleotide to the phosphoramidite solution or modification solution for a few seconds, the solution is displaced by a fresh batch of monomer solution. In the case of coupling with phosphoramidites, the support is washed before oxidation or thiation (sulphurisation). In the case of coupling with the modified monomers of formula 1, where Z is a group of formula II, also known as phosphonamidites, the support is immediately exposed to the oxidation or thiation solution with no wash cycle. This procedure minimises potential hydrolysis of the support bound PIII intermediate.

In the nucleotide sequences for the modified oligonucleotides given below, T, C, A and G have their usual significance and are derived from the usual phosphoramidite monomers, t denotes a nucleotide unit derived from Compound 5 and c denotes a nucleotide unit derived from Compound 7, Compound 5 and Compound 7 being used at the appropriate points in the syntheses. Sulphurised internucleotide linkages are denoted by s; all other internucleotide linkages are oxidised.

EXAMPLE 9

5' TTTTtCTCTCTCTCT 3'

TOF MS Found =
Required = 4424.3

EXAMPLE 10

5' tttttCTCTCTCTCT 3'

TOF MS Found = 4415.3
Required = 4415.9

EXAMPLE 11

5' GCGttttttttttGCG 3'

TOF MS Found = 4859.8
Required = 4865

EXAMPLE 12

5' TTTTTTTTTTTTTTTtttT 3'

TOF MS Found = 5709.3
Required = 5711.7

EXAMPLE 13

5' ttctcG$_s$C$_s$C$_s$C$_s$G$_s$C$_s$T$_s$C$_s$C$_s$tcctcC 3'

TOF MS  Found = 6086.6
Required = 7001.5

EXAMPLE 14

5' tstscstscsGsCsCsCsGsCsTsCsCstscscstscsC 3'

TOF MS  Found = 6214.5
Required = 6246.1

EXAMPLE 15

5' tstscstscsGsCsTsGsGsTsGsAsGststststscsA 3'

TOF MS  Found = 6092.9
Required = 6114

---

What is claimed is:

1. A compound of formula

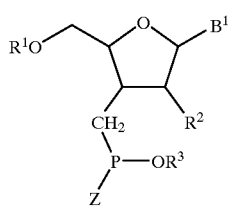

I where $B^1$ is a radical of a nucleoside base, $R^1$ is hydrogen or a hydroxy-protecting group, $R^2$ is hydrogen, hydroxy or a 2' nucleoside-modifying atom or group, $R^3$ is an unsubstituted or substituted $C_1$ to $C_{10}$ alkyl, $C_2$ to $C_{10}$ alkenyl, $C_4$ to $C_{10}$ cycloalkylalkyl, $C_6$ to $C_{10}$ aryl or $C_7$ to $C_{13}$ aralkyl group, and Z is halogen or a group of formula

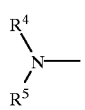

II where $R^4$ and $R^5$ are each independently an unsubstituted or substituted $C_1$ to $C_{10}$ alkyl, $C_2$ to $C_{10}$ alkenyl, $C_4$ to $C_{10}$ cycloalkylalkyl, $C_6$ to $C_{10}$ aryl or $C_7$ to $C_{13}$ aralkyl group, or $R^4$ is said group and $R^5$ is hydrogen, or $R^4$ and $R^5$ together with the nitrogen atom to which they are attached denote a five- to thirteen-membered heterocyclic ring, or Z is a group of formula Nuc—O—   III where Nuc is the residue of a natural or synthetic nucleoside or oligonucleotide after removal of a 5'-hydroxyl group therefrom attached through a 5' methylene thereof to the indicated oxygen atom.

2. A compound according to claim 1, wherein the substituted groups are substituted by halogen, hydroxy, $C_1$–$C_4$ alkoxy, cyano, nitro or tri ($C_1$–$C_{15}$ hydrocarbyl) silyl.

3. A compound according to claim 1, wherein $R^1$ is hydrogen, a $C_7$ to $C_{40}$ araliphatic group or a tri ($C_1$–$C_{15}$ hydrocarbyl)silyl group.

4. A compound according to claim 3, wherein $R^1$ is hydrogen, an unsubstituted or substituted triphenylmethyl group or $C_1$–$C_6$ alkyldi ($C_6$–$C_8$ aryl) silyl group.

5. A compound according to claim 4, wherein $R^1$ is a dimethoxytrityl or tert-butyldiphenylsilyl group.

6. A compound according to claim 1, wherein $R^2$ is hydrogen, halogen, hydroxy or a group of formula —$OR^6$ or —$OCOR^6$ where $R^6$ is an unsubstituted or substituted $C_1$ to $C_{10}$ alkyl, $C_2$ to $C_{10}$ alkenyl, $C_3$ to $C_8$ cycloalkyl, $C_4$ to $C_{10}$ cycloalkylalkyl, $C_6$ to $C_{10}$ aryl or $C_7$ to $C_{25}$ aralkyl group or a tri ($C_1$–$C_{15}$ hydrocarbyl) silyl group.

7. A compound according to claim 6, wherein $R^2$ is hydrogen, hydroxy, fluorine, a group of formula —$OR^6$ where $R^6$ is a $C_1$ to $C_4$ alkyl group, a $C_2$ to $C_4$ alkenyl group, a $C_7$ to $C_{13}$ aralkyl group, or a group of formula —($R^7$—O—)$_n$—$R^8$ where $R^7$ is $C_1$ to $C_4$ alkylene, $R^8$ is $C_1$ to $C_4$ alkyl and n is 1 to 8; or $R^2$ is a group of formula —$OCOR^6$ where $R^6$ is $C_1$ to $C_4$ alkyl or $C_6$ to $C_8$ aryl.

8. A compound according to claim 6, wherein $R^2$ is hydrogen, hydroxy, fluorine, methoxy, ethoxy, allyloxy, benzyloxy, methoxyethoxy, $-O-(CH_2-CH_2-O-)_3-CH_3$, acetoxy or benzoyloxy.

9. A compound according to claim 1, wherein $R^3$ is an unsubstituted or substituted $C_1$ to $C_4$ alkyl, $C_3$ to $C_5$ alkenyl, $C_6$ to $C_8$ cycloalkylalkyl or $C_7$ to $C_9$ aralkyl group.

10. A compound according to claim 9, wherein $R^3$ is methyl, ethyl, 2-cyanoethyl, 2,2,2-trichloroethyl, allyl, benzyl or 2-(trimethylsilyl) ethyl.

11. A compound according to claim 1, in which Z is a group of formula

II wherein $R^4$ and $R^5$ are independently an unsubstituted or substituted $C_1$ to $C_4$ alkyl, $C_3$ to $C_5$ alkenyl, $C_6$ to $C_8$ cycloalkylalkyl or $C_7$ to $C_9$ aralkyl group, or $R^4$ is $C_1$ to $C_4$ alkyl or $C_7$ to $C_9$ aralkyl and $R^5$ is hydrogen, or $R^4$ and $R^5$ together with the attached nitrogen atom denote a five- or six-membered heterocyclic ring having one or two heteroatoms in the ring.

12. A compound according to claim 11, wherein $R^4$ and $R^5$ are independently methyl, ethyl, n-propyl, isopropyl, n-butyl, sec-butyl, isobutyl, tert-butyl, allyl or benzyl or $R^4$ and $R^5$ together with the attached nitrogen atom denote a pyrrolidine, piperidine or morpholine ring.

13. A compound according to claim 1, wherein Z is a group of formula

Nuc-O— III in which Nuc is attached to a solid support.

14. A compound according to claim 1, wherein Z is chlorine or bromine.

15. A compound according to claim 1, which is of formula

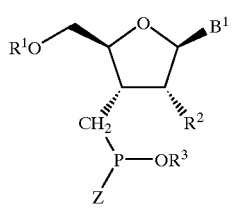

IV where $B^1$ is a radical of a nucleoside base, $R^1$ is a hydrogen or a hydroxy-protecting group, $R^2$ is a hydrogen, hydroxy or a 2' nucleoside-modifying atom or group, $R^3$ is an unsubstituted or substituted $C_1$ to $C_{10}$ alkyl, $C_2$ to $C_{10}$ alkenyl, $C_4$ to $C_{10}$ cycloalkylalkyl, $C_6$ to $C_{10}$ aryl or $C_7$ to $C_{13}$ aralkyl group, and Z is halogen or a group of formula

II where $R^4$ and $R^5$ are each independently an unsubstituted $C_1$ to $C_{10}$ alkyl, $C_2$ to $C_{10}$ alkenyl, $C_4$ to $C_{10}$ cycloalkylalkyl, $C_6$ to $C_{10}$ aryl or $C_7$ to $C_{13}$ aralkyl group, or $R^4$ is said group and $R^5$ is hydrogen, or $R^4$ and $R^5$ together with the nitrogen atom to which they are attached denote a five- to thirteen-membered heterocyclic ring, or Z is a group of formula Nuc-O— III where Nuc is the residue of a natural or synthetic nucleoside or oligonucleotide after removal of a 5'-hydroxyl group therefrom attached through a 5' methylene thereof to the indicated oxygen atom.

16. A compound according to claim 1 wherein $B^1$ is thyminyl, 5-methylcytosinyl or thyminyl or 5-methylcytosinyl substituted on a nitrogen atom by a protecting group; $R^1$ is dimethoxytrityl or tert-butyldiphenylsilyl; $R^2$ is hydrogen; $R^3$ is methyl, ethyl or 2-cyanoethyl; and Z is chlorine or a group of formula

II where $R^4$ and $R^5$ are each methyl or isopropyl or Z is a group of formula Nuc-O— III where Nuc is the residue of a natural or synthetic nucleoside or oligonucleotide after removal of a 5'-hydroxyl group therefrom attached through a 5' methylene thereof to the indicated oxygen atom.

17. A method of preparing a compound according to claim 1 wherein Z is a group of formula

II which comprises the step of:
reacting a compound of formula

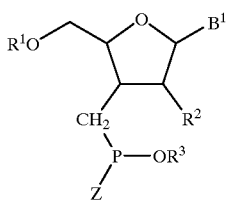

I in which Z is halogen with a compound of formula

VI where $R^4$ and $R^5$ are each independently an unsubstituted or substituted $C_1$ to $C_{10}$ alkyl, $C_2$ to $C_{10}$ alkenyl, $C_4$ to $C_{10}$ cycloalkylalkyl, $C_6$ to $C_{10}$ aryl or $C_7$ to $C_{13}$ aralkyl group, or $R^4$ is said group and $R^5$ is hydrogen, or $R^4$ and $R^5$ together with the nitrogen atom to which they are attached denote a five- to thirteen-membered heterocyclic ring.

18. The method of claim 17, wherein the reaction is carried out in an organic solvent in the presence of a tertiary nitrogen base at a temperature from −78° C. to 50° C.

19. A method of preparing a compound of formula

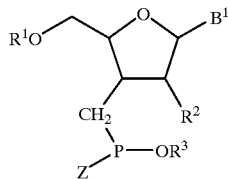

I wherein Z is halogen comprising the steps of:

non-oxidatively halogenating a compound of formula

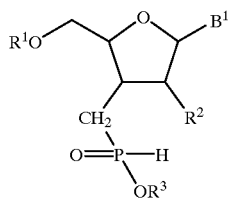

VII where $B^1$ is a radical of a nucleoside base, $R^1$ is hydrogen or a hydroxy-protecting group, $R^2$ is hydrogen, hydroxy or a 2' nucleoside-modifying atom or group, and $R^3$ is an unsubstituted or substituted $C_1$ to $C_{10}$ alkyl, $C_2$ to $C_{10}$ alkenyl, $C_4$ to $C_{10}$ cycloalkylalkyl, $C_6$ to $C_{10}$ aryl or $C_7$ to $C_{13}$ aralkyl group with a non-oxidative halogenating agent.

20. A method according to claim 19, wherein the non-oxidative halogenating agent is a halophosphorane.

21. A method according to claim 19, wherein the halogenation is carried out in the presence of a base in an organic solvent at a temperature from −20° C. to 60° C.

22. A method of preparing a compound of formula

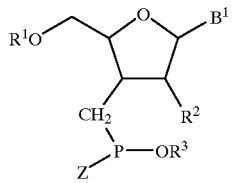

I wherein Z is a group of formula

 Nuc-O—

III the method comprising the step of:

reacting the compound of formula I where where $B^1$ is a radical of a nucleoside base, $R^1$ is a hydroxy-protecting group, $R^2$ is hydrogen, hydroxy or a 2' nucleoside-modifying atom or group, $R^3$ is an unsubstituted or substituted $C_1$ to $C_{10}$ alkyl, $C_2$ to $C_{10}$ alkenyl, $C_4$ to $C_{10}$ cycloalkylalkyl, $C_6$ to $C_{10}$ aryl or $C_7$ to $C_{13}$ aralkyl group and Z is a group of formula

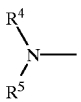

II where $R^4$ and $R^5$ are each independently an unsubstituted $C_1$ to $C_{10}$ alkyl, $C_2$ to $C_{10}$ alkenyl, $C_4$ to $C_{10}$ cycloalkylalkyl, $C_6$ to $C_{10}$ aryl or $C_7$ to $C_{13}$ aralkyl group, or $R^4$ is said group and $R^5$ is hydrogen, or $R^4$ and $R^5$ together with the nitrogen atom to which they are attached denote a five- to thirteen-membered heterocyclic ring, with a natural or synthetic nucleoside or oligonucleotide having a free 5' hydroxyl group.

23. A method of preparing an oligonucleotide of formula

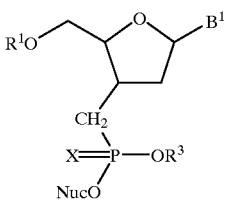

VIII where $B^1$ is a radical of a nucleoside base, $R^1$ is hydrogen or a hydroxy-protecting group, $R^3$ is an unsubstituted or substituted $C_1$ to $C_{10}$ alkyl, $C_2$ to $C_{10}$ alkenyl, $C_4$ to $C_{10}$ cycloalkylalkyl, $C_6$ to $C_{10}$ aryl or $C_7$ to $C_{13}$ aralkyl group and Nuc is the residue of a natural or synthetic nucleoside or oligonucleotide after removal of a 5'-hydroxyl group therefrom attached through a 5' methylene thereof to the indicated oxygen atom and X is oxygen or sulfur, wherein the method comprises the step of:

subjecting a compound according to formula

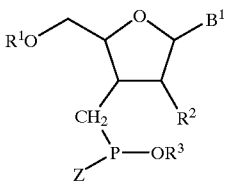

I where $R^2$ is hydrogen, hydroxy or a 2' nucleoside-modifying atom or group and where Z is a group of formula

 Nuc-O—

III where Nuc is the residue of a natural or synthetic nucleoside or oligonucleotide after removal of a 5'-hydroxyl group therefrom attached through a 5' methylene thereof to the indicated oxygen atom, to oxidation to give an oligonucleotide of formula VIII where X is oxygen or to sulphurisation to give an oligonucleotide of formula VIII where X is sulphur.

24. A method of preparing an oligonucleotide comprising the step of:

subjecting a nucleoside having a protected 5' hydroxy group and, at the 3' position, a group of formula

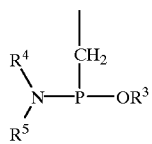

IX where $R^3$ is an unsubstituted or substituted $C_1$ to $C_{10}$ alkyl, $C_2$ and $C_{10}$ alkenyl, $C_4$ to $C_{10}$ cycloalkylalkyl, $C_6$ to $C_{10}$ aryl or $C_7$ to $C_{13}$ aralkyl group, $R^4$ and $R^5$ are each independently an unsubstituted $C_1$ to $C_{10}$ alkyl, $C_2$ to $C_{10}$ alkenyl, $C_4$ to $C_{10}$ cycloalkylalkyl, $C_6$ to $C_{10}$ aryl or $C_7$ to $C_{13}$ aralkyl group, or $R^4$ is said group and $R^5$ is hydrogen, or $R^4$ and $R^5$ together with the nitrogen atom to which they are attached denote a five- to thirteen-membered heterocyclic ring, to a nucleoside coupling reaction with a natural or synthetic nucleoside or oligonucleotide having a free 5' hydroxy group, to form an oligonucleotide precursor having an internucleoside linkage of formula

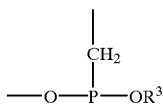

X and converting the precursor into an oligonucleotide having an intenucleoside linkage of formula

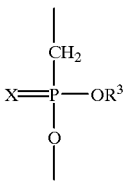

XI where X is oxygen or sulphur by oxidising the precursor to give an oligonucleotide having an intenucleoside linkage of formula XI where X is oxygen or sulphurising the precursor to give an oligonucleotide having an internucleoside linkage of formula XI where X is sulphur.

* * * * *

SEQUENCE LISTING

<160> NUMBER OF SEQ ID NOS: 6

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 1
tttttctctc tctct                                                        15

<210> SEQ ID NO 2
<211> LENGTH: 11
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 2
tctctctctc t                                                            11

<210> SEQ ID NO 3
<211> LENGTH: 16
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 3
gcgttttttt tttgcg                                                       16

-continued

```
<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 4
tttttttttt tttttttt                                                 19

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 5
ttctcgcccg ctcctcctcc                                               20

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 6
ttctcgctgg tgagtttca                                                19
```